United States Patent [19]

Chambers

[11] 4,349,018
[45] Sep. 14, 1982

[54] OSTEOTOMY APPARATUS

[76] Inventor: Gary R. Chambers, 705 McFarland St., Morristown, Tenn. 37814

[21] Appl. No.: 221,015

[22] Filed: Dec. 29, 1980

[51] Int. Cl.³ .............................................. A61B 17/18
[52] U.S. Cl. ............................... 128/92 E; 128/303 R; 30/293
[58] Field of Search ........... 128/92 EB, 92 E, 92 EC, 128/305, 317, 303 B, 303 R; 30/293

[56] References Cited

U.S. PATENT DOCUMENTS

| | | | |
|---|---|---|---|
| 2,200,120 | 5/1940 | Nauth | 128/92 EB |
| 2,737,724 | 3/1956 | Herz | 128/92 EB |
| 4,037,592 | 7/1977 | Kronner | 128/92 EB |

Primary Examiner—Michael H. Thaler
Attorney, Agent, or Firm—Pitts & Kesterson

[57] ABSTRACT

Surgical apparatus for use in guiding and aligning a surgical blade or osteotome for bone removal from the tibia and femur during a proximal tibia osteotomy or a total knee replacement operation is disclosed. The apparatus includes a femur "T" bar unit and a tibia "T" bar unit which are connected to the shaft of the femur and tibia bones respectively. First and second guide members provide means such that desired or selected cutting planes can be maintained during the bone cutting operation. These guides may be selectively attached to the mid portion of the T-bar units for providing a guide for total knee replacement or to the lateral or medial ends of the "T"-bar for a proximal tibia osteotomy. The medial and lateral ends of the cross bars of the T-bar units are secured to each other by means which are selected according to the operation to be performed. That is, a selection is made depending on whether the operation is to be a proximal tibia osteotomy or a total knee replacement. Although this apparatus is suitable for both, of particular importance is the use of this apparatus for a proximal tibia osteotomy in that an accurate measurement of the necessary correction may be determined and then a section or wedge of bone precisely removed to exactly achieve the necessary correction.

11 Claims, 20 Drawing Figures

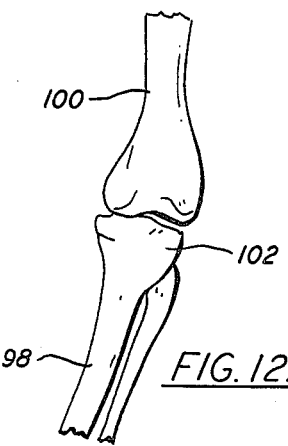
FIG. 12A
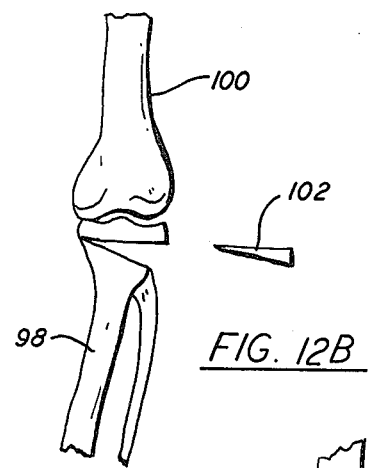
FIG. 12B
FIG. 12C
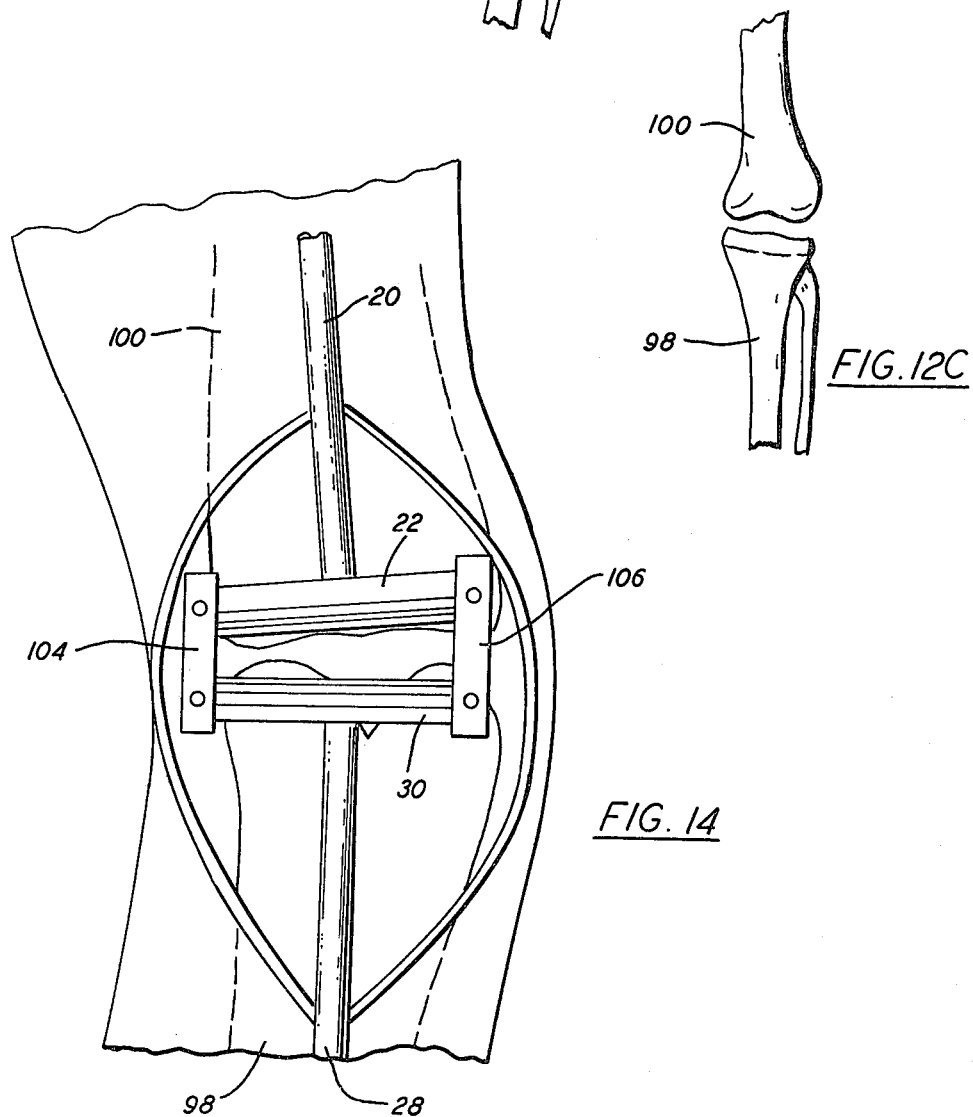
FIG. 14

OSTEOTOMY APPARATUS

BACKGROUND OF THE INVENTION

This invention relates to surgical apparatus suitable for use during tibia/femur osteotomy for total knee replacement, or a proximal tibia osteotomy for corrective knee structuring. More specifically, the apparatus of this invention is universal in that means are provided for precisely maintaining a cutting plane, precisely determining the necessary amount of bone to be removed and for guiding osteotome blade for precisely removing such amount of bone.

Osteotomy is an operation upon bone which involves cutting the bone and sometimes removing or adding portions of the bone and also includes moving bone parts in space relative to one another. In a similar manner, prosthetic surgery often involves the excision and removal of deteriorated and diseased bone tissue in either the knee and hip joints and has now become quite common. In many instances, artifical members of plastic and/or metal which is compatible with the body systems are substituted for the removed natural bone. Such artifical members or joints are available for both knee and hip bone structures.

In particular, the bearing surface of the knee joint is vulnerable to stress, arthritic and other disease induced deterioration. Prosthetic correction is indicated when the tissue becomes so damaged that other less drastic techniques have little or no prospect of success. Thus, there has been developed various surgical techniques ranging from corrective surgery all the way to total knee replacement. In particular, surgery which is somewhat less extensive than total knee replacement includes "high tibia osteotomy". High tibia osteotomy or proximal tibia osteotomy is particularly useful where a patient has a varus deformity of the knee. That is, one or both knees bow outward at an angle significantly greater than the desired valgus position of 5 to 8 degrees. A proximal tibia osteotomy may be specifically performed to change from a varus to a valgus position of 5 to 8 degrees and thereby shift the weight bearing load of the knee from the medial to the lateral compartment. This type of corrective surgery also achieves a smooth congrous osteotomy surface and avoids violation of the knee joint itself. In practice to date, there has been significant problems and factors which detrimentally affect the clinical judgement in the operating room such that very accurate proximal tibia osteotomys are difficult to obtain. For example, recent articles presented to the AAOS (American Association of Orthapedic Surgeons) indicate difficulties with osteotomy procedures because of factors which affect the clinical judgement of the surgeon in the operating room. In particular, an article entitled *High Tibial Osteotomy Revisited* written by Dr. James J. Elting, Dr. William R. Hopper, and Dr. Larene E. Lane, of the Aurelia Osburn Fox Memorial Hospital in Oneonta, N.Y. points out some of the difficulties with respect to the osteotomy procedure. For example, on page 1, the article states that "precise measurements of the femoral-tibial angle is impossible either roentgenograhically or clinically" and at page 2 that "precise measurement is impossible, by any means". Thus, it is seen that sucessful surgeons are willing to present medical papers to their peers admitting to the difficulty or the impossibility of obtaining precise measurements in proximal tibia osteotomy surgery. However, as will be discussed hereinafter, the present invention allows precise measurements rather than depending upon rules of thumb such as a one millimeter of bone wedge to be removed per degree of correction". Other factors affecting the clinical judgement include the thickness of the soft tissue and the magnification caused by x-ray etc. Thus, it will be appreciated that any kind of technique or apparatus which provides precise measurement to determine the wedge of bone to be removed during a proximal tibia corrective osteotomy would be a major advancement in such surgical techniques.

It would be of particular value if such an apparatus suitable for providing precise measurements for proximal tibia osteotomys could also be used as standard equipment for total knee replacement osteotomys. Thus, the surgeon would become more familiar with the equipment. Although an investigation of the available prior art failed to reveal any type of apparatus relevant to the present invention, several patents that were discovered are discussed hereinafter, and may be referred to for reference as typical types of apparatus. For example, U.S. Pat. No. 3,728,742 issued to Robert G. Averill et al. on Apr. 24, 1973 discloses a total knee or elbow prosthesis. According to this patent the complete knee or elbow joint may be replaced with metal or plastic type components if the original joint has been destroyed by arthritis or other disease or accident. Reference to this patent will reveal the type of surgical bone removal that must take place for such total knee replacement as is also discussed in the present invention.

In addition, measuring devices used to insert a pin in a hip bone is described in U.S. Pat. No. 4,037,592 issued to Richard F. Kronner on July 26, 1977. This device provides a tool and method such that surgeons may carefully insert a hip nail guide pin within the upper end of the femur. Earlier nail guides for the femur include one disclosed in the U.S. Pat. No. 2,200,120 issued to W. W. Nauth on May 7, 1940 and U.S. Pat. No. 2,737,724 issued to J. R. Herz on Mar. 13, 1956. Reference to these patents quickly indicates that in no way are they relative to osteotome blade guides useful in a proximal tibia osteotomy or a total knee replacement osteotomy. However, these patents do show that measuring devices are useful and accepted by surgeons when they can be directly used to take the guess work out of a surgery technique.

In addition to the above discussed patents, other references may be had to apparatuses available from the Zimmer Company of Warsaw, Ind. which provides surgical apparatus, or the Orthopedics Division of Howmedical, Inc. which also provides apparatus for total knee replacements and proximal tibia osteotomys. Reference to all of these materials clearly indicates that even with the use of presently available apparatus, a great deal of clinical judgement and guess work is required in the operating room during the osteotomy surgery.

SUMMARY OF THE INVENTION

It is an object of the present invention to provide apparatus which allows for precise measurement and removal of a bone wedge during a proximal tibia osteotomy.

It is another object of the present invention to provide apparatus suitable for use both for corrective proximal tibia osteotomys and total knee replacement osteotomys.

It is yet another object of the present invention to remove the necessity of clinical judgement and guess work due to variations in soft tissue surrounding a knee or other parameters which may vary with different patients, and with the particular osteotomy techniques.

To accomplish the above objects as well as others, the present invention discloses surgical apparatus suitable for use in both a tibia/femur total knee osteotomy and a proximal tibia osteotomy. The apparatus includes a femur "T" unit having an elongated femur rod, one end of which is connected to the mid portions of a femur bar to form said "T" unit. The two portions are securely joined such that there is an angle between the bar and the rod of between 80 and 100 degrees. According to one embodiment a permanent angle of between 80 and 100 degrees is selected whereas according to a second embodiment the angle selection may be adjustable according to the wishes of the surgeon. In addition, the femur "T" unit includes a pin, nail or screw which is used to secure the "T" unit to the front portion of the femur such that the elongated rod is parallel to the femur and the elongated bar is substantially perpendicular to the bone. A similar tibia "T" unit also includes an elongated tibia rod and an elongated tibia bar. However, with respect to the tibia "T" unit, one end of the tibia rod is permanently mounted to the mid portion tibia bar at substantially a right angle and need not be adjustable. The cross section of both the femur and tibia bars are suitable for receiving femur and tibia guide units. These guide units include mounting means such that they may be mounted to the mid-portion of the tibia and femur bars for total knee osteotomy or they may be attached to one end of the femur and tibia bars for proximal tibia osteotomy. The guide units typically include slots for receiving an osteotome blade. Proper mounting of the guides to the femur and tibia bars, results in the slots providing a cutting plane which intersect the length of a patients leg at the desired position. During the performance of a proximal tibia osteotomy, (to correct from a varus to a valgus position) the medial ends of the bars are secured at a selected angle which has its apex at the medial cortex of the tibia itself.

The tibia and femur guide members are then attached to the lateral ends of the bars such that a precise wedge shaped section of bone may be removed from the proximal end of the tibia. Prior to removal of the precise section of bone, the amount of correction is determined and then by simply removing the proper amount of bone, the correction is achieved. With respect to a total knee replacement osteotomy, the two lateral ends and the two medial ends of the bars are carefully spaced with respect to each other at the proximal end of the tibia and the distal end of the femur. The two guides which may be the same as the guides discussed heretofore with respect to a proximal tibia osteotomy are then secured to the middle portion of the two bars such that the correct amount of bone from both the tibia and the femur can be removed so that the joint can receive a prosthetic knee joint device. Thus, as will be discussed in detail hereinafter it can be seen that the same precise measuring apparatus may be used for both a proximal tibia osteotomy and a total knee replacement osteotomy.

BRIEF DESCRIPTION OF THE DRAWINGS

FIG. 3 shows the femur "T" bar unit of FIG. 1 with an adjustable mounting between the femur rod and the femur bar.

FIG. 3A shows an alternate means of attaching the femur rod to the femur bar.

FIG. 3B shows to examples of removable pins suitable for use as tibia or femur pins.

FIG. 4 shows interchangeable guides suitable for guiding an osteotome blade, which guides may be used for both proximal tibia osteotomys and total knee replacement osteotomys.

FIG. 4A shows an alternate mounting of the guide of FIG. 4 for a total knee replacement osteotomy.

FIGS. 12A, 12B and 12C show a series of three frontal bone views during the progression of a proximal tibia osteotomy.

FIG. 14 shows the apparatus of FIG. 8 in place on a human leg for performing a total knee replacement osteotomy.

DETAILED DESCRIPTION OF THE INVENTION

Figure 1:
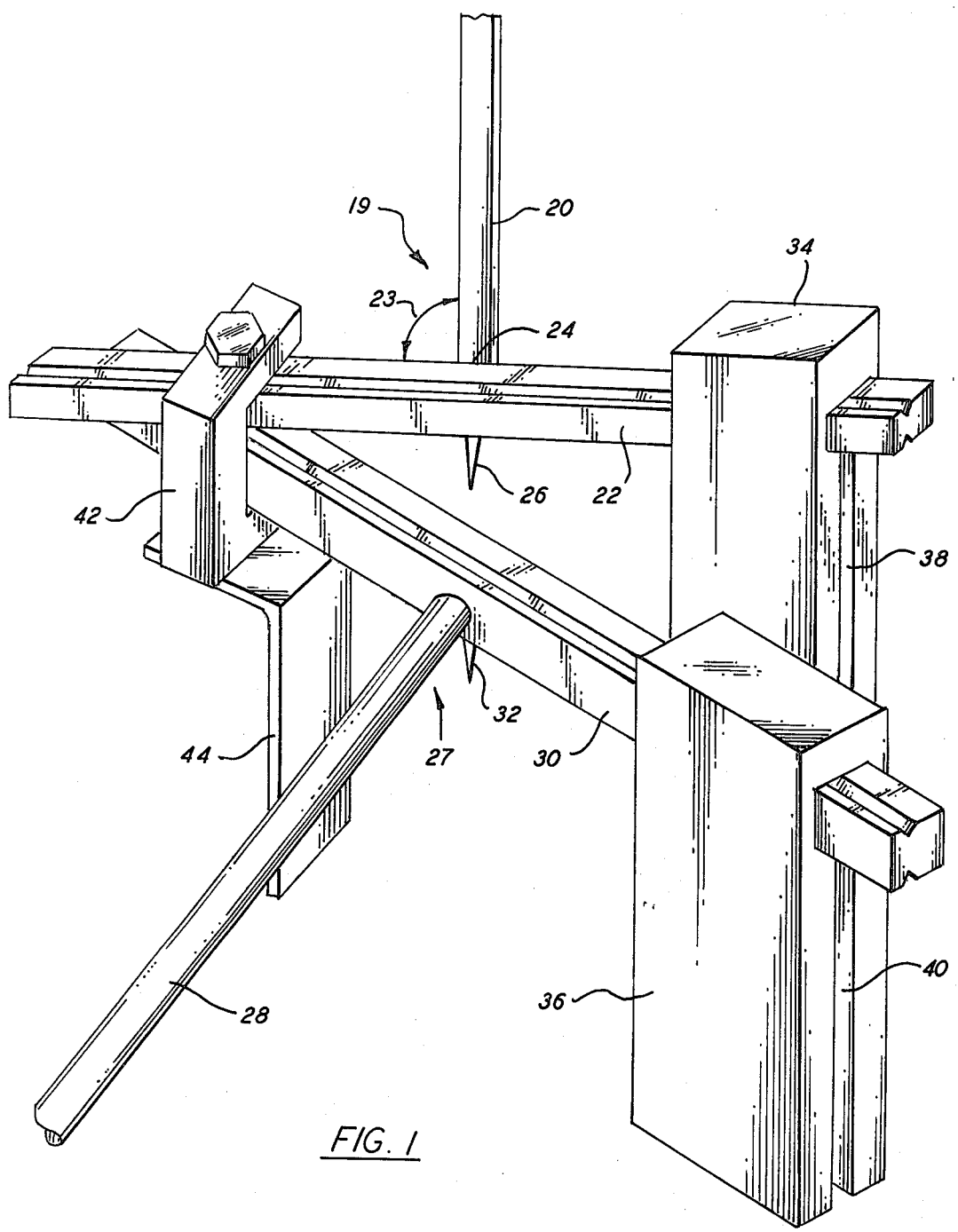
FIG. 1 shows the precise measuring apparatus of this invention as it is arranged for a proximal tibia osteotomy.

Referring now to FIG. 1 there is shown a perspective view of one embodiment of the precise measuring apparatus of this invention as it is arranged for a proximal tibia osteotomy. Included in this apparatus is a femoral "T" unit 19 which includes a femoral rod 20 which is securely attached to a femoral bar 22. Although the femoral rod 20 and femoral bar 22 may be of substantially any cross section, it will be appreciated that the femoral bar unit 22 is preferably about a one centimeter square, and the femoral rod 20 may be a one half to one centimeter round or a one half by one centimeter flat shaped bar. End 24 of the femoral rod 20 is securely and rigidly attached to the femoral bar unit 22, however, the angle between the femoral rod 20 and the femoral bar 22 may vary, but is typically at an 82 degree angle as shown by arrow 23 to provide an 8° valgus correction on the left knee. Although the femoral rod 20 and the femoral bar 22 may be at a permanent selected angle such as 82°, it will be appreciated, and will be discussed in detail hereinafter, that according to another embodiment the angle between the two may be adjustably selected to provide for a 0° to 10° valgus or varus correction according to the desires of the surgeon. Also included is a pin 26 which is driven into the bone. For example, pin 26 may be driven into the tibia during a proximal tibia osteotomy or the femur in a total knee replacement as will be discussed hereinafter. Pin 26 may be a replaceable nail, screw or other means which is ing at a selected location suitable for receiving the bar unit. Locking screws 76 and 78 are used to secure the guide unit to the mid portion of the bar. The end view of the guide 34 in FIG. 4A shows how a channel 80 may be permanently welded to the guide unit for additional strength rather than the two parallel plates as discussed with respect to the embodiment of FIG. 4.

Referring again to FIG. 1, to achieve a precise alignment of the apex 43 of the angle between the bars 22 and 30 at the medial cortex of the patients tibia, clamp 42 is shown for clamping the two bars at a selected location. Tibial plate 44 is attached to clamp 42, and rests against the medial portion of the patients knee. It will be noticed that tibia plate 44 is offset such that apex 43 between the two bars may actually be aligned with the media cortex of the patients tibia no matter how much soft tissue is common to the patient.

Figure 5:
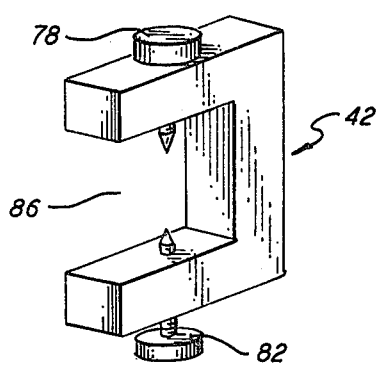
FIG. 5 shows a clamp for use with the apparatus of this invention during a proximal tibia osteotomy.
Figure 6:
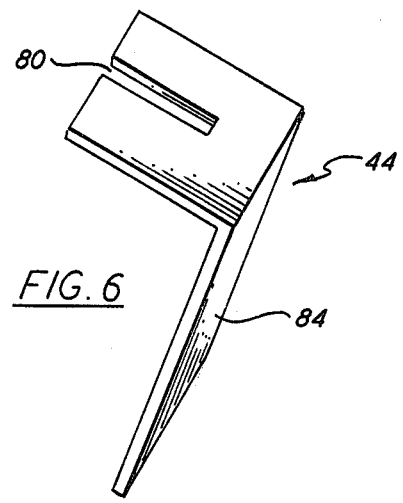
FIG. 6 is a tibia plate for use with the clamp of FIG. 5.

Referring now to FIGS. 5 and 6, there are shown isolated perspective views of the clamp 42 and tibia plate 44 of FIG. 1. Also shown in FIG. 7, and as will be discussed hereinafter, there is another embodiment or technique for joining the ends of a tibia bar and femur bar when they are used for a proximal tibia osteotomy. In addition FIGS. 8, 9 and 10 illustrate other types of tibia plates 44.

As shown is shown in FIG. 5, clamp 42 of FIG. 1, may simply be a study "C" shaped clamp having a thumb screw 78 for securing the tibia and femur bars together. FIG. 6 shows tibia plate 44 having a slot 80 which is adjustably attached to clamp 42 by means of another thumb screw 82. Thus, it can be seen that by simply adjusting plate 44 along slot 80, leg 84 of plate 44 can be positioned against the medial portion of the patients leg no matter how much soft tissue is common to the patient.

Figure 7:
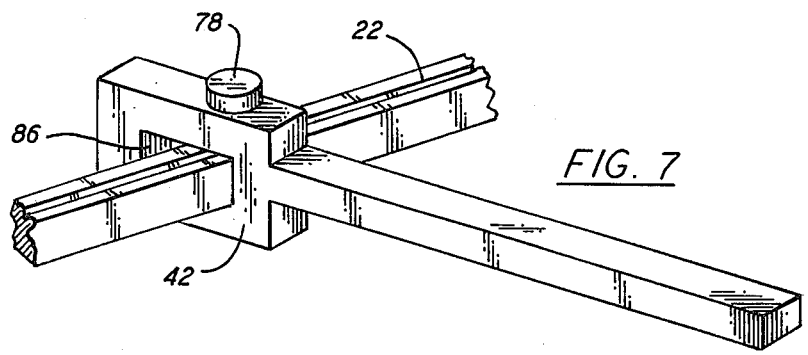
FIG. 7 is an alternate method of joining the tibia and femur bars for a proximal tibia osteotomy.

As shown in FIG. 7, clamp 42 is made as an intergal part of tibia rod 30, and aperature 86 is suitable for receiving only a single bar (femur 22) rather than two bars was the case for aperature 86 of FIG. 5. It will also be appreciated that clamp 42 of FIG. 7 is closed. That is, it is not a "C" shaped clamp as shown in FIG. 5. It will be appreciated, however, that the clamp 42 of FIG. 5 could alternately be closed as shown in FIG. 7, or the closed clamp 42 of FIG. 7 could be a "C" clamp such as shown in FIG. 5.

Figure 8:
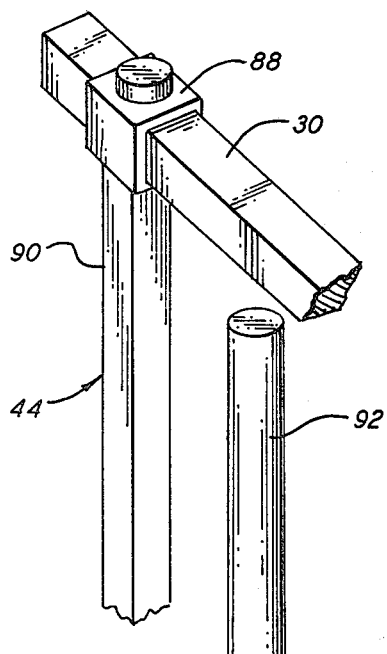
FIGS. 8, 9 and 10 show alternate embodiments of tibia plates.
Figure 9:
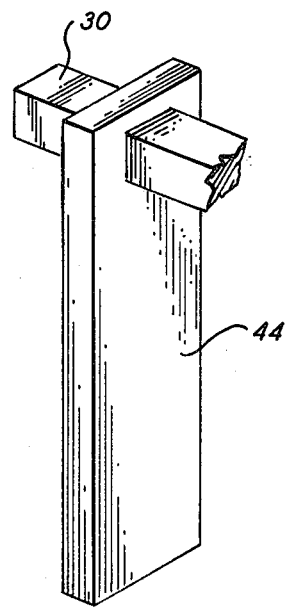
Figure 10:
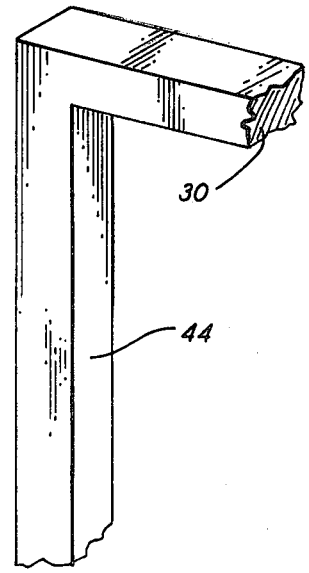
Figure 11:
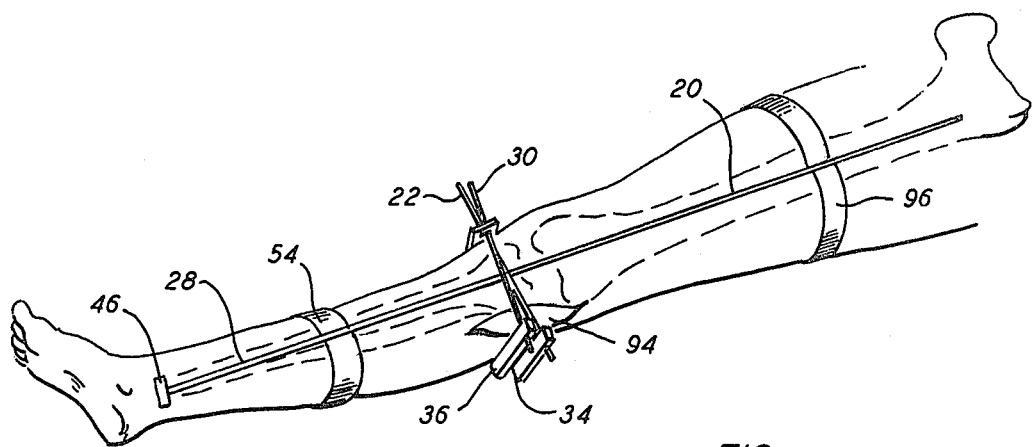
FIG. 11 shows a prospective view of the apparatus of FIG. 1 in place on a leg in preparation for a proximal tibia osteotomy.

FIGS. 8, 9 and 10 show alternate embodiments of tibia plate 44. As shown in FIG. 8, tibia plate 44 includes a mounting sleeve which slides on tibia bar 30 such that plate 44 can be moved along bar 30 so that it is in firm contact with the medial portion of the patient knee. Also as shown, the portion that rests against the patients knee may be a square member 90, or alternately a round cross-shaped member such as shown at 92. FIG. 9 shows a plate having an aperature which serves as plate 44, and FIG. 10 shows a simplified embodiment, wherein plate 30 is simply a right angle extension of tibia bar 30. Total Knee Replacement Osteotomy Referring now to FIG. 11, there is shown a sketch of the apparatus of FIG. 1 in place on a patients leg wherein the incision 94 on the lateral side of the patients knee is shown and the patients tibia and femur are in outline form to show the alignment of the femur rod 20 and the tibia rod 28 with respect to the bones in the patients leg. Thus, from the illustration of FIG. 5 it can be seen how the apparatus is securely mounted to the patients leg by means of the femur pin 26, the tibia pin 32, and the spring clamps 54 and 96.

Referring now to FIGS. 12A through 12C there are shown a series of three frontal views of the patients tibia 9B and femur 100 as a proximal tibia osteotomy progress. These figures show the wedged shaped section 102 of the tibia 86 being removed from the patient and the remaining bone then aligned to correct from a deformed varus to a proper valgus condition. From the foregoing, it can be seen that apparatus has been discussed which allows a precise wedge of bone to be removed from a patients tibia without violation of the knee joint itself and which apparatus removes the need for guess work during the surgical procedure.

Figure 13:
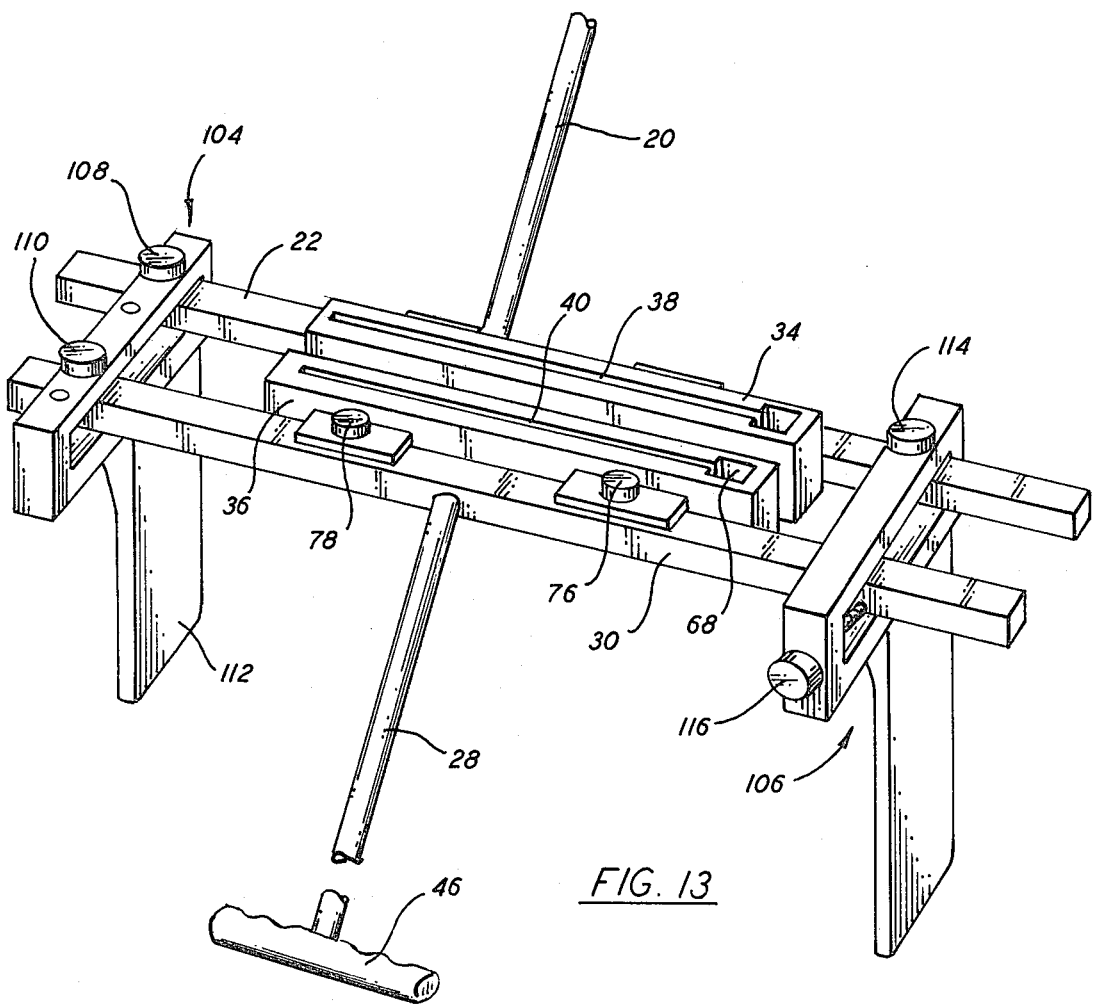
FIG. 13 shows the precise measuring apparatus of this invention as it is arranged for a total knee replacement osteotomy.

Referring now to FIG. 13, there is shown the precise measuring device of this invention in an arrangement suitable for a total knee replacement osteotomy. As seen, those portions of the apparatus which were common with respect to the proximal tibia osteotomy have similar reference numerals. Actually, the only difference between the apparatus of FIG. 1 and FIG. 13 is that the guide units 34 and 36 are no longer mounted at the lateral ends of bars 22 and 30 respectively, but are mounted at the mid portions of bars 22 and 30 such that the osteotome blade may remove bone from both the proximal end of the tibia and the distal end of the femur. Also as can be seen, instead of the guide units 36 and 34 being mounted such that the aperature 68 receives the ends of bars 22 and 30, the two pairs of parallel plates 72 and 74 are used to mount the guide units to the bar units 22 and 30. Thus, the cutting plane as defined by the slot 38 and 40 is substantially perpendicular to the patients leg through the knee joint. In addition, rather than using the clamp unit 42 and tibia plate 44 as discussed heretofore, the apparatus when used for a total knee replacement osteotomy includes mounting clamps 104 and 106 which provides for precise selection of the distance between the two bars 22 and 30 at both the medial and lateral side of a patients knee. Referring now to FIG. 14, there is shown a sketch of the apparatus of FIG. 13 in place with respect to the patients leg and knee prior to the performance of the osteotomy procedure. As shown, the knee joint of the patient is exposed and the tibia "T" unit is permanently attached to the tibia and the femur unit is pemanently attached to the femur. The clamp units 104 and 106 secure the two bars 22 and 30 at a selected distance from each other at both the medial and lateral portions of the patients knee. As can also be seen, the slots 38 and 40 for the osteotome blade are located such that the blade is in position to remove the proximal end of the patients tibia and the distal end of the patients femur.

Referring again to FIG. 13, there is shown an embodiment of a clamp means 104 suitable for use with the apparatus of this invention for a total knee replacement osteotomy. As seen, the bar units 22 and 30 are secured at selected distances from each other in the clamp 104 by locking thumb screws 108 and 110. In the embodiment shown, the bar unit 22 is always mounted in the same position and is held in place by locking screw 104, whereas the bar 30 may be located in one of three positions by simply moving locking screw 110 to the proper location. Thus, there is shown three precise selectable distances between the bars 22 and 30. As shown in FIG. 13, it is seen that clamp 104 also includes an extension 112 which may be used as a retractor. Thus, when the clamp is mounted to the two bar units 22 and 30, extension 112 extends into the interior of the patients knee and serves as a retractor to maintain all of the soft tissue away from the bone as the osteotomy proceeds. Furused to securely attached the "T" bar unit to the bone of the patient prior to the surgery.

In addition to the femur "T" unit 19, there is also a tibia "T" unit 27 which is constructed substantially similar. The tibia "T" unit 27 includes a tibia rod 28 and a tibia bar 30. The tibia rod is permanently or securely attached to the tibia bar 30 such that a right angle of substantially 90 degrees is maintained between the two. According to the embodiment shown in FIG. 1, the tibia rod and the tibia bar forming the tibia "T" unit, are permanently welded together such that the angle between the two is not adjustable. However, as will be discussed herinafter various techniques for mounting the rod to the bar may be used to provide versatility. Also included with the tibia "T" unit 27 is a tibia pin 32 similar to the femur pin 26 which was discussed heretofore.

A pair of guide units 34 and 36 are attached to the femur bar 22 and the tibia bar 30 respectively. As shown, apertures in the guide units 34 and 36 have the same cross section as the bars 22 and 30 respectively, such that these apertures can receive the bar 22 and 30. Slot 38 in guide unit 34 and slot 40 in guide unit 36 establish a pair of cutting planes such that an osteotome blade may be inserted in the slots and properly guided with respect to the bone such that the proper wedge shape of bone may be removed. To obtain the precise wedge shape measurement, and assuming the illustration of FIG. 1 is set up to correct from a varus to a valgus condition on the left knee, it will be appreciated that the guides 34 and 36 are on the lateral ends of the bars 22 and 30 and that the medial ends of the bars are brought together at a selected angle. The selected angle between the femur bar 22 and tibia bar 30 is precisely set to the number of degrees of corrective surgery desired. That is, if an 8° varus to valgus correction is desired, then the angle between the bar 22 and 30 will also be set at 8°. The selected angle between the two bars is held in place by a clamp 42 to which is attached tibia plate 44 which rests against the inside or medial portion of the patients knee. As will be shown hereinafter with respect to FIG. 7, clamp 42 may be adjusted with respect to bars 22 and 30 and each patient such that the apex 43 of the angle between the bars 22 and 30 is aligned with the medial cortex of the tibia itself. Thus, the portion of bone removed is zero at the medial cortex portion of the bone and then progresses at the selected angle to a wedge shaped portion having its larger dimension at the lateral cortex of the tibia.

Figure 2:
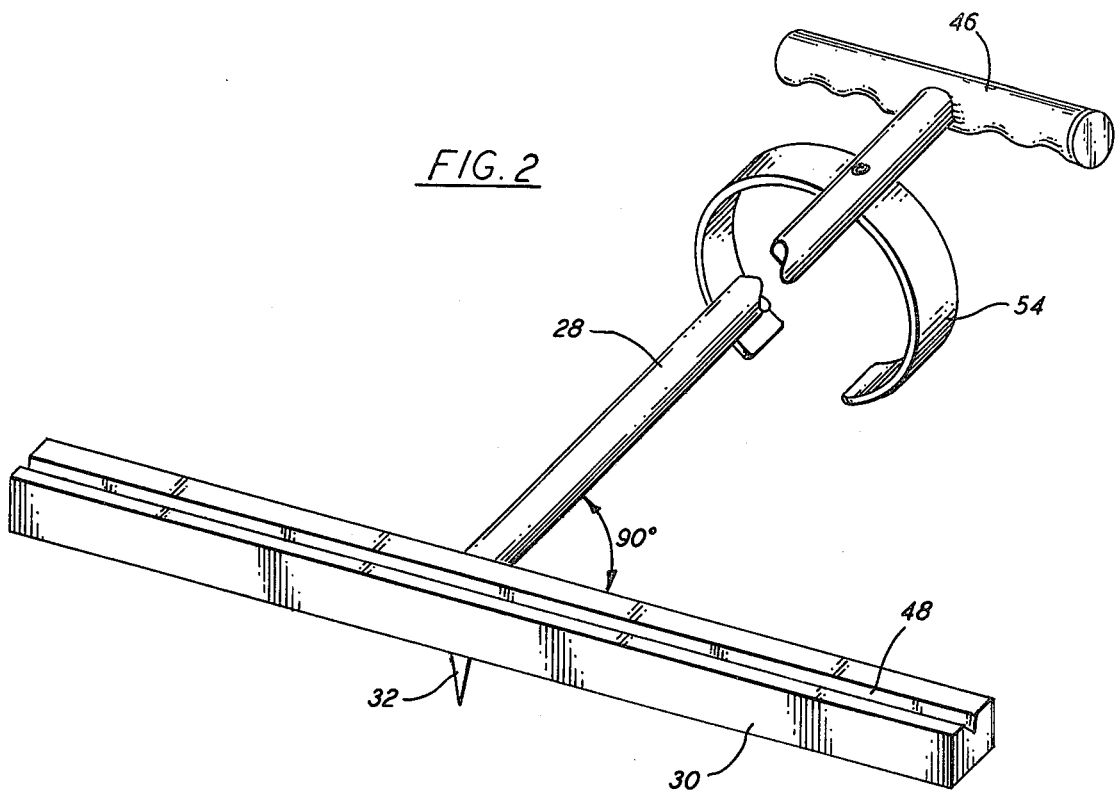
FIG. 2 shows the tibia "T" bar unit of the apparatus shown in FIG. 1.
Figure 2A:
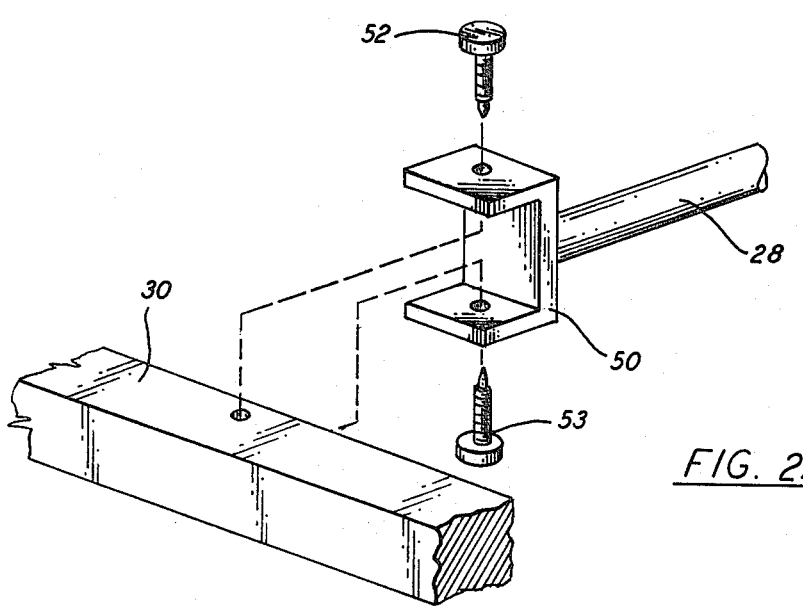
FIG. 2A shows an embodiment for removably attaching the tibia and rod to the tibia bar.

Referring now to FIG. 2, there is shown a perspective view of the tibia "T" bar unit. According to this unit, rod 28 which would typically be approximately 30 centimeters is shown to be permanently mounted to bar 30 at a 90 degree angle. Also shown is a handle 46 which may be used during the surgical operation to place the desired amount of stress on the ligaments etc. Also as shown in FIG. 2, the tibia bar member 30 includes a V-shaped groove 48 suitable for receiving a set screw for securely mounting the guide units 34 and 36 to bars 22 and 30 as will be discussed hereinafter. Also included is Tibia pin 32 which may be removeable, or alternately bar 30 (or 22) may include a hole for a drill such that a screw may be mounted through bar 30 (or 22) into the bone. Although the embodiment of FIG. 2 shows the rod 28 permanently secured to bar 30, it will be appreciated that various attaching techniques could be included. Therefore, as is shown in FIG. 2A, there is shown a technique by which rod unit 28 includes a mounting means 50 permanently secured thereto, which mounting means slidely fits the bar 30. Tightening screws 52 and 53 allows the means to be secured to the bar 30. In addition to handle 46, as shown in FIG. 2, the end of rod 28 opposite bar 30 may also include a spring clamp 54 which holds the "T" bar unit to the patients leg during the surgical procedure.

Referring now to FIG. 3, there is shown a partial perspective view of the femur "T" bar unit. As shown in the embodiment of FIG. 3, the femur rod 20 is flat and includes index pointer 56 at its end which mounts to the bar member. As shown, there is also a locking screw 58 by which the bar unit 20 may be selectively adjusted to a desired angle on mounting member 60. In the embodiment shown, mounting member 60 includes indicia representative of an angle ranging from 0 to 10 degrees in either direction such that the surgeon may select the angle between the bar and the rod as desired for making either a varus or valgus correction. Also included on the mounting member 60 is a second locking screw such that the bar 22 may be securely attached to rod 20 in the same manner as was discussed heretofore with respect to FIG. 2A. FIG. 3A shows still another alternant embodiment whereby a channel receives the bar 22 and thereby provides even additional strength. It will be appreciated of course, that the tibia "T" unit as discussed above could also use a channel for detachably mounting the bar and rod. As was the case with respect to the tibia "T" bar unit discussed heretofore, the femur pin 26 may be made removeable such that it may be replaced with various styles of pins or replaced when it becomes dull and not effective. FIG. 3B shows two types of femur pins which are suitable and which will also be suitable for use with the tibia bar unit.

Referring now to FIG. 4, there is shown a particular embodiment of an osteotome guide such as guides 34 or 40 discussed with respect to FIG. 1. The unit shown in FIG. 4 is substantially the same as guide unit 34 or 36 as discussed heretofore with respect to FIG. 1 except that the slot 38 in the guide of FIG. 4 is a closed slot as whereas the slot in the FIG. 1 device is open at ends 64 and 66. FIG. 4 shows a perspective view of the guide unit. It will be appreciated, of course, that the common components of the guide unit of FIG. 4 and FIG. 1 also include the same reference number. As shown in FIG. 4, the guide unit has a substantially elongated boxed shape, which includes an osteotome blade slot 38 through one of its dimensions. Also included is an enlarged area 68 which is suitable for receiving the bars 22 and 30 when the guide unit is used for a proximal tibia osteotomy. As shown, a thumb screw 70 is included for purposes of attaching the guide unit to the respective bar for a proximal tibia osteotomy such that it is tightly secured. Also shown, in FIG. 4, an osteotome blade 71 maybe inserted in slot 30 such that blade 71 is maintained at a precise cutting plane so that the proper amount of bone can thereby be removed. As was discussed heretofore, the guide units may either be used for a proximal tibia osteotomy or for a total knee replacement osteotomy. In the event the surgery is to be a total knee replacement osteotomy, the guide units further include means for mounting the guide to the mid-portion of the femur or tibia bars 22 or 30 respectively to obtain a different cutting plane. These mounts are shown in the embodiment of FIG. 4 as two pairs of parallel plates 72 and 74. As shown means 72 and 74 consist of two pairs of parallel plates securely mounted such as by welding casting, or other permanent mountther, as stated above, in the embodiment shown in FIG. 13, it can be seen that the space between bars 22 and 30 may be selected by varying the location of locking thumb screw 110. The space between bars 22 and 30 may preferably be selected to be 7.5 millimeters, 12.5 millimeters and finally 15 millimeters.

However, in some instances it may be desireable to have even a finer adjustment than these three distinct selections. Thus, there is shown clamp means 106 which includes a vernier adjustment such that the distance between bar 22 and 30 may be varied to an infinite desired amount. As shown thumb screw 14 still clamps bar 22 securely, but vernier screw 116 allows any selected adjustment of bar 30 with respect to bar 22. Although clamps 104 and 106 of FIG. 13 have been discussed as been used as a medial and lateral clamps respectively, it will be appreciated that either clamp may be used for the lateral side or the medial side of the patients knee.

From FIGS. 13 and 14 it is clear how the guide 84 and 36 allow bone to be selectively removed from both the tibia and femur, such that a total knee prosthetic device can be installed to replace a patients natural knee.

Thus, there has been discussed surgical apparatus which provides precise measurement and control for a cutting plane and which is suitable for use for both a corrective proximal tibia osteotomy, and a total knee replacement osteotomy wherein the knee joint of a patient is replaced by a prosthetic device. In addition, it will be appreciated that the apparatus discussed herein provides preciseness in the surgical techniques.

While there have been described what are at present considered to be preferred embodiments of this invention, it will be obvious to those skilled in the art that various changes and modifications may be made therein without departing from the invention, and it is, therefore, intended to cover all such changes and modifications as fall within the true spirit and scope of this invention.

I claim:

1. Surgical apparatus useful for both a tibia-femur osteotomy and a proximal tibia osteotomy comprising:
   a femur "T" unit including an elongated femur rod having a first and further end and an elongated femur bar having a mid portion and a medial and lateral end, said first end of said rod being securely joined to said mid-portion of said bar to form a substantially "T" shaped unit such that said "T" unit has an angle between said bar and said rod of between 80 degrees and 100 degrees, and said femur "T" unit further includes a femur pin secured to said femur "T" unit for securing said femur "T" unit to a selected bone of a patient such that said elongated rod is parallel to the selected bone and said elongated bar is substantially perpendicular to the selected bone;
   a tibia "T" unit including an elongated tibia rod having a first and further end and an elongated tibia bar having a mid-portion, and a medial and a lateral end, said first end of said tibia rod being joined to said mid-portion of said tibia bar to form a "T" shaped unit, said rod and said bar having substantially a right angle there between, and also including a tibia pin secured to said tibia "T" unit for securing said tibia "T" unit to a selected bone of a patient such that said elongated rod is parallel to the selected bone and said bar is substantially perpendicular to the selected bone;
   a femur and tibia guide unit, said femur guide unit suitable for guiding an osteotome blade along a first selected plane, and said tibia guide unit suitable for guiding said ostetome blade along a second selected plane, said guide units suitable for being detachably mounted to said femur and tibia bars respectively such that said first and second selected planes intersect the length of a patient's leg at first and second locations respectively, said femur and tibia guide units suitable for mounting to the mid part of said femur and tibia bars for performing an osteotomy for total knee replacement, and suitable for mounting to said medial and lateral ends of said femur and tibia bars for preforming a proximal tibia osteotomy.

2. The surgical apparatus of claim 1 wherein said femur pin is suitable for securing said femur "T" unit to the distal end of a patient's femur, said tibia pin is suitable for securing said tibia "T" unit to the proximal end of a patients tibia, and said femur guide and tibia guide units are mounted to the mid portion of said femur bar and said tibia bar respectively, and further including:
   means for securing the medial ends of said tibia and femur bars at a first selected distance from each other; and
   means for securing the lateral ends of said tibia and femur bars at a second selected distance from each other such that said first and second planes are located at a selected location with respect to each other so that a precise osteotomy of a patient's tibia and femur can be accomplished for total knee joint replacement.

3. The surgical apparatus of claim 2 wherein one of said means for securing said medial end and said means for securing said lateral ends of said bars include means for adjusting said selected distance between said femur bar and said tibia bar.

4. The surgical apparatus of claim 2 or 3 wherein one of said means of securing includes an extended portion for serving as a retractor during performing of a total needle knee replacement osteotomy.

5. The surgical apparatus of claim 1 wherein said femur pin is suitable for securing to the proximal end of a patient's tibia, said tibia pin is also suitable for securing to the proximal end of a patient's tibia below said femur pin, and said femur and tibia guide units are mounted to one of said medial and lateral ends of said femur and tibia bars and further including:
   means for joining one of said medial and lateral ends of said femur bar unit and said tibia bar unit such that said first and second planes intersect at a selected angle at one of the medial and lateral cortex of a patients tibia so that a precise wedge section of bone may be removed to accomplish a precise proximal tibia osteotomy.

6. The sugical apparatus of claim 1, 2 or 5 and further including femur or tibia spring clamps mounted to said further ends of said femur and tibia rods respectively for clamping said rod to a patients leg.

7. The surgical apparatus of claim 1, 2 or 5 wherein said femur pin and tibia pin are detachably mounted to said femur "T" unit and said tibia "T" unit respectively.

8. The surgical apparatus of claim 1, 2 or 5 wherein said tibial rod includes a handle at said further end.

9. The surgical apparatus of claims 1, 2 or 5 wherein said femur and tibia guide units each include a slot corresponding to said first and second selected planes and for receiving and guiding an osteotome blade.

10. The surgical apparatus of claims 1, 2, or 5 wherein said angle between said femur rod and femur bar may be adjustably selected.

11. The surgical apparatus of claim 5 wherein said means for joining include means for clamping said femur bar and tibia bar together and further includes a tibia plate.

* * * * *